(12) United States Patent
Sawada et al.

(10) Patent No.: US 7,602,479 B2
(45) Date of Patent: Oct. 13, 2009

(54) LIGHT EMISSION MEASURING APPARATUS AND LIGHT EMISSION MEASURING METHOD

(75) Inventors: Ryuji Sawada, Hachioji (JP); Yoshio Nakashima, Hino (JP)

(73) Assignee: Olympus Corporation, Tokyo (JP)

( * ) Notice: Subject to any disclaimer, the term of this patent is extended or adjusted under 35 U.S.C. 154(b) by 244 days.

(21) Appl. No.: 11/666,629

(22) PCT Filed: Nov. 1, 2005

(86) PCT No.: PCT/JP2005/020130

§ 371 (c)(1),
(2), (4) Date: Jul. 25, 2007

(87) PCT Pub. No.: WO2006/049180

PCT Pub. Date: May 11, 2006

(65) Prior Publication Data

US 2007/0257182 A1 Nov. 8, 2007

(30) Foreign Application Priority Data

Nov. 1, 2004 (JP) ............................. 2004-318351

(51) Int. Cl.
*G02B 21/00* (2006.01)
*G01N 21/63* (2006.01)
*G01N 21/64* (2006.01)

(52) U.S. Cl. ..................... 356/72; 356/317; 356/318; 356/417; 250/458.1

(58) Field of Classification Search ................ 356/72, 356/73, 317, 318, 417
See application file for complete search history.

(56) References Cited

FOREIGN PATENT DOCUMENTS

| JP | 04-138341 | * | 5/1992 |
| JP | 2003-185928 | | 7/2003 |
| JP | 2003-207450 | | 7/2003 |
| JP | 2003-524180 | | 8/2003 |
| JP | 2004-69795 | | 3/2004 |

* cited by examiner

*Primary Examiner*—F. L Evans
(74) *Attorney, Agent, or Firm*—Scully, Scott, Murphy & Presser, P.C.

(57) ABSTRACT

A light fluctuation measuring apparatus, comprising a parameter setting unit 2 which sets parameters of a microscopic image obtaining unit and/or parameters of a light emission measuring unit used for observing light emission in a desired area of a sample in time series, a parameter storage 4 which stores parameters, a mode selector 3 which selects one of a microscopic image obtaining mode for obtaining a microscopic image by a microscopic image obtaining unit, and a light emission measuring mode for observing light emission in a desired area by a light emission measuring unit, and a control unit 1 which reads parameters stored in the storage 4 based on a selected mode, inputs the parameter to a microscopic image obtaining unit or a light emission measuring unit, and controls these units.

29 Claims, 6 Drawing Sheets

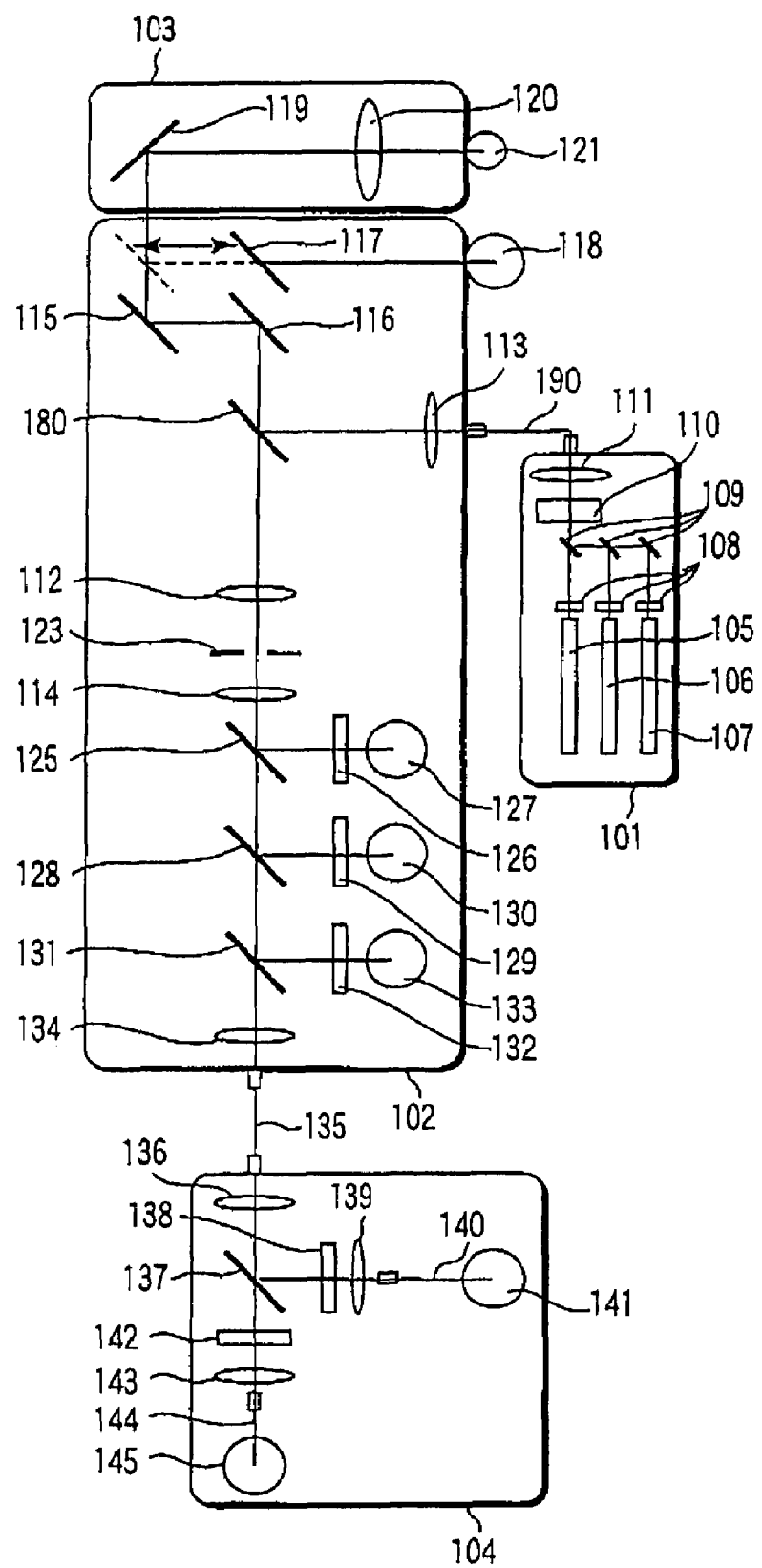
F I G. 3

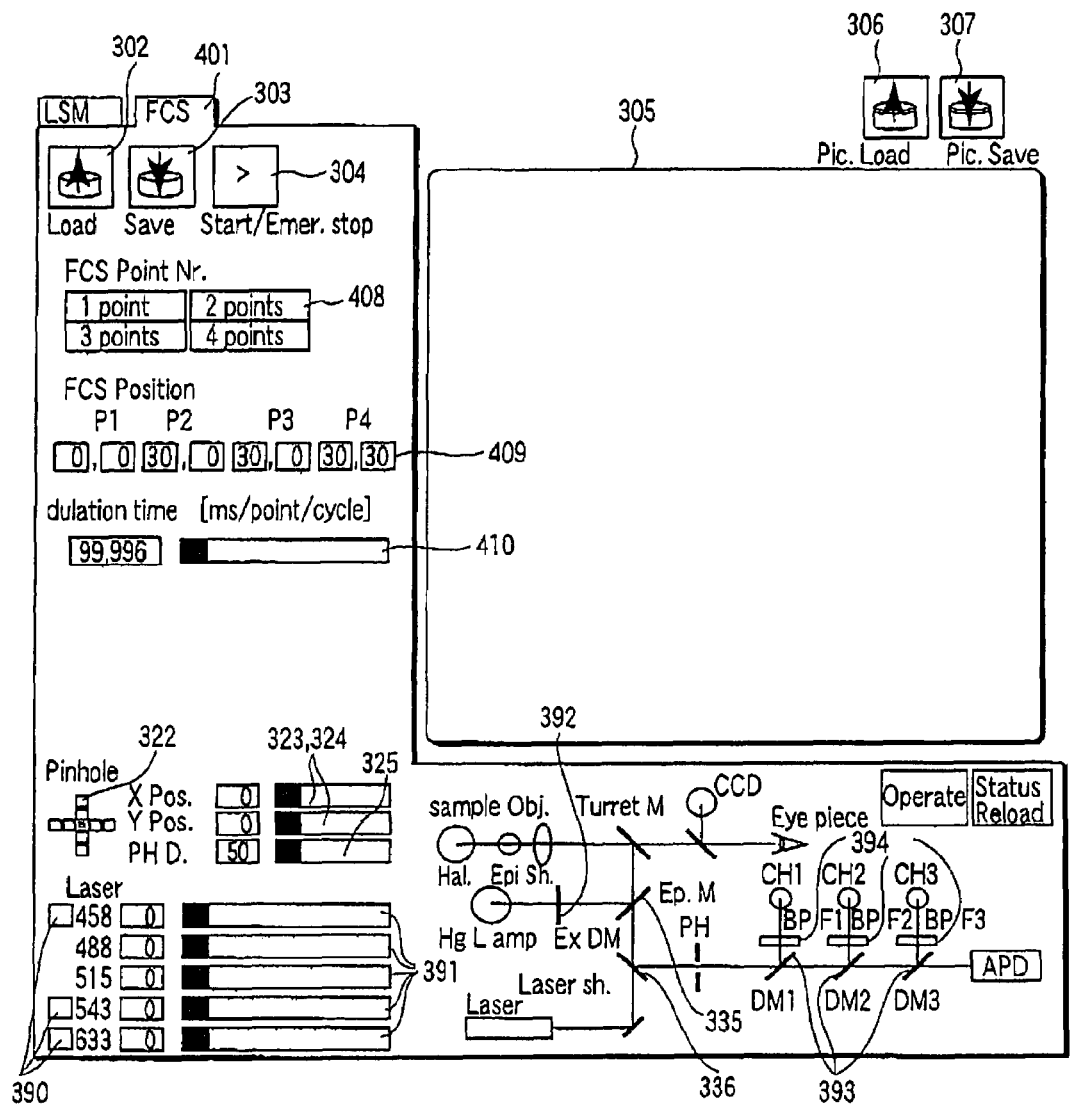
F I G. 6

LIGHT EMISSION MEASURING APPARATUS AND LIGHT EMISSION MEASURING METHOD

CROSS REFERENCE TO RELATED APPLICATION

This application is a U.S. national phase application under 35 USC 371 of International Application PCT/JP2005/020130 (not published in English), filed Nov. 1, 2005, the contents of which is incorporated herein by reference.

TECHNICAL FIELD

The present invention relates to a light emission measuring apparatus, such as a light emission fluctuation measuring apparatus, and a light emission measuring method.

BACKGROUND ART

About fluorescence correlation spectroscopy will be explained hereinafter as an analysis example of fluctuation of fluorescence that is an example of light emission. Fluorescence correlation spectroscopy has been discussed in "Fluorescence Correlation Spectroscopy" R. Rigler, E. S. Elison (eds.) Springer (Berlin), "Protein, Nucleic Acid, Enzyme" (1999) Masataka Kinjo Vo. 44, No, p1431-1437, and PCT National Publication No. 11-502608. An apparatus for fluorescence correlation spectroscopy is often manufactured on the basis of a confocal optical microscope. A confocal optical microscope has been discussed in "Confocal Microscopy" T. Wilson (ed.) Academic press (London). A laser scanning confocal optical microscope that is a kind of confocal optical microscope may be used as a basis. A laser scanning confocal optical microscope has been described in Japanese Patent Laid-Open Publication No. 10-206742. When an apparatus for fluorescence correlation spectroscopy is combined with a confocal optical microscope, statistic analysis operation such as correlation spectroscopy can be performed while observing or recording a fluorescent microscopic image.

PCT National Publication No. 2003-524180 discloses the switching of a fluorescence correlation spectroscope (FCS) and a laser scanning microscope (LSM) in a fluorescence detecting apparatus and method.

DISCLOSURE OF INVENTION

In correlation analysis of fluorescence at an optional point on a sample, a method of specifying an optional measuring point by a laser scanning microscopic image and obtaining a fluorescence correlation analysis value at that point is desired. Settings of filter, optical path and laser intensity used in optics of an analyzing apparatus are generally different for obtaining a microscopic image and measuring a fluorescence correlation. However, there is no conventional system for automatically reproducing settings of optics for obtaining a microscopic image and optics for measuring a fluorescence correlation. Therefore, whenever obtaining a microscopic image and measuring a fluorescence correlation are switched, the operator must change many settings of optics by himself. This makes the operation complex, and takes much time.

The present invention has been made to solve the above problems. Accordingly, it is an object of the invention to provide a light emission fluctuation measuring apparatus and method capable of improving convenience in switching measurement of a microscopic image and measurement of fluorescence fluctuation.

According to a first aspect of the present invention, there is provided a light emission measuring apparatus for observing and measuring light emission from a sample as an observation object in time series, comprising:

a microscopic image obtaining unit which obtains a microscopic image of a sample under conditions set based on input parameters;

a light emission measuring unit which observes light emission in a desired area of the sample corresponding to the microscopic image in time series under conditions set by input parameters;

a parameter setting unit which sets parameters of the microscopic image obtaining unit used for obtaining the microscopic image and/or parameters of the light emission measuring unit used for observing light emission in a desired area of the sample in time series;

a parameter storage which stores parameters set by the parameter setting unit;

a mode selector which selects one of a microscopic image obtaining mode for obtaining the microscopic image by the microscopic image obtaining unit, and a light emission measuring mode for observing light emission in the desired area by the light emission measuring unit; and a control unit which reads parameters stored in the storage based on a mode selected by the mode selector, inputs the parameter to the microscopic image obtaining unit or the light emission measuring unit, and controls the microscopic image obtaining unit and/or the light emission measuring unit.

According to a second aspect of the present invention, there is provided a light emission measuring apparatus according to a first aspect, wherein the light emission measuring apparatus measures fluctuation of light emission.

According to a third aspect of the present invention, there is provided a light emission measuring apparatus according to a first aspect, wherein the light emission is fluorescence.

According to a fourth aspect of the present invention, there is provided a light emission measuring apparatus according to a third aspect, wherein the microscopic image obtaining unit is a laser scanning microscope unit.

According to a fifth aspect of the present invention, there is provided a light emission measuring apparatus according to a fourth aspect, wherein the laser scanning microscope unit is a confocal type.

According to a sixth aspect of the present invention, there is provided a light emission measuring apparatus according to a third aspect, wherein the parameters input to the microscopic image obtaining unit are parameters related to optics of the microscopic image obtaining unit.

According to a seventh aspect of the present invention, there is provided a light emission measuring apparatus according to a sixth aspect, wherein the parameters input to the microscopic image obtaining unit are parameters related to a lens and/or a filter and/or a pinhole of the microscopic image obtaining unit.

According to an eighth aspect of the present invention, there is provided a light emission measuring apparatus according to a third aspect, wherein the parameters input to the microscopic image obtaining unit are stored in the parameter storage at the end of microscopic image obtaining mode.

According to a ninth aspect of the present invention, there is provided a light emission measuring apparatus according to a third aspect, wherein the parameters input to the microscopic image obtaining unit are read from the parameter storage at the start of the microscopic image obtaining mode.

According to a tenth aspect of the present invention, there is provided a light emission measuring apparatus according to a third aspect, wherein the parameters related to the light emission measuring unit input to the parameter storage are interlocked with setting of the microscopic image obtaining unit.

According to an eleventh aspect of the present invention, there is provided a light emission measuring apparatus according to a third aspect, wherein the parameters input to the light emission measuring unit are parameters related to optics of the light emission measuring unit.

According to a twelfth aspect of the present invention, there is provided a light emission measuring apparatus according to an eleventh aspect, wherein the parameters input to the microscopic image obtaining unit are parameters related to optics defining an observation area of the microscopic image obtaining unit.

According to a thirteenth aspect of the present invention, there is provided a light emission measuring apparatus according to an twelfth aspect, wherein the observation area is more than one.

According to a fourteenth aspect of the present invention, there is provided a light emission measuring apparatus according to an eleventh aspect, wherein the parameters input to the light emission measuring unit are parameters related to a lens and/or a filter and/or mirror and/or AOTF and/or a pinhole of the light emission measuring unit.

According to a fifteenth aspect of the present invention, there is provided a light emission measuring apparatus according to a third aspect, wherein the parameters input to the light emission measuring unit are stored in the parameter storage at the end of the light emission measuring mode.

According to a sixteenth aspect of the present invention, there is provided a light emission measuring apparatus according to a third aspect, wherein the parameters input to the light emission measuring unit are read from the parameter storage at the start of the light emission measuring mode.

According to a seventeenth aspect of the present invention, there is provided a light emission measuring apparatus according to a third aspect, wherein the parameters related to the microscopic image obtaining unit input to the parameter storage are interlocked with setting of the light emission measuring unit.

According to an eighteenth aspect of the present invention, there is provided a light emission measuring apparatus according to a third aspect, wherein when the parameters related to the microscopic image obtaining unit are changed, a display is made for confirming a changed input to the light emission measuring unit at the start of the light emission measuring mode.

According to a nineteenth aspect of the present invention, there is provided a light emission measuring apparatus according to a third aspect, wherein the microscopic image obtaining unit and light emission measuring unit share a part of optics.

According to a twentieth aspect of the present invention, there is provided a light emission measuring apparatus according to a nineteenth aspect, wherein the parameters input to the microscopic image obtaining unit and light emission measuring unit include parameters related to optics shared by the microscopic image obtaining unit and light emission measuring unit.

According to a twenty-first aspect of the present invention, there is provided a light emission measuring apparatus according to a third aspect, wherein the parameter setting unit includes an observing position setter for setting a light emission observing area according to the microscopic image.

According to a twenty-second aspect of the present invention, there is provided a light emission measuring apparatus according to a third aspect, further comprising an output unit for displaying or printing observation results.

According to a twenty-third aspect of the present invention, there is provided a light emission measuring apparatus according to a twenty-second aspect, wherein the output unit performs the display by relating to parameters.

According to a twenty-fourth aspect of the present invention, there is provided a light emission measuring apparatus according to a third aspect, further comprising a data processor for performing time correlated operations.

According to a twenty-fifth aspect of the present invention, there is provided a light emission measuring apparatus according to a twenty-second aspect, comprising a display unit for displaying results of the time correlated operations as a graph.

According to a twenty-sixth aspect of the present invention, there is provided a light emission measuring apparatus according to a twenty-fifth aspect, wherein the graph takes a correlation value on a vertical axis, and a delay time on a horizontal axis.

According to a twenty-seventh aspect of the present invention, there is provided a light emission measuring apparatus according to a twenty-fifth aspect, wherein the display unit performs the display by correlating with any one of the parameters.

According to a twenty-eighth aspect of the present invention, there is provided a light emission measuring method for observing and measuring light emission from a sample as an observing object in time series, comprising:

a microscopic image obtaining step for obtaining a microscopic image of a sample under conditions set based on input parameters;

a light emission measuring step for observing light emission in a desired area of the sample corresponding to the microscopic image in time series under conditions set by input parameters;

a parameter setting step for setting parameters of the microscopic image obtaining unit used for obtaining the microscopic image and/or parameters of the light emission measuring unit used for observing light emission in a desired area of the sample in time series;

a parameter storing step for storing parameters set in the parameter setting step;

a mode selecting step for selecting one of a microscopic image obtaining mode for obtaining the microscopic image in the microscopic image obtaining step, and a light emission measuring mode for observing light emission in the desired area in the light emission measuring step; and a control step for reading parameters stored in the storing step based on a mode selected by the mode selecting step, and controlling the microscopic image obtaining step and/or the light emission measuring step.

According to a twenty-ninth aspect of the present invention, there is provided a light emission measuring apparatus according to a twenty-eighth aspect, wherein the light emission measuring method includes measuring fluctuation of the light emission.

BRIEF DESCRIPTION OF DRAWINGS

FIG. 3 is a diagram showing the optics of a fluorescence fluctuation measuring apparatus according to an embodiment of the invention;

FIG. 6 is a view showing an operation screen of a fluorescence fluctuation measuring apparatus according to an embodiment of the invention, indicating the state that an FCS operation panel is placed on the front side.

BEST MODE FOR CARRYING OUT THE INVENTION

Figure 1:
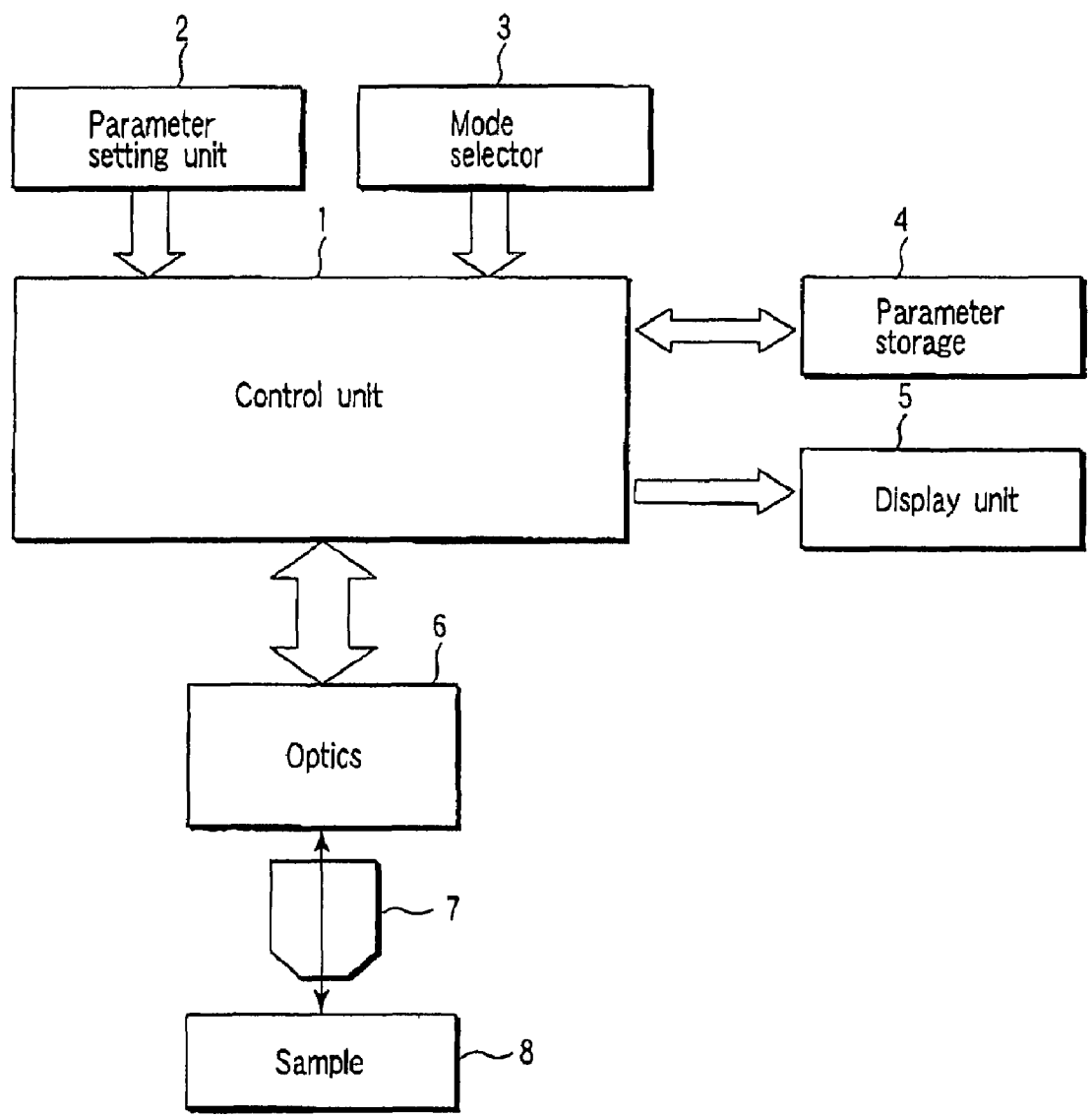
FIG. 1 is a diagram showing a basic configuration of a light emission measuring apparatus according to the invention.

Embodiments of the invention will be explained in detail hereinafter with reference to the accompanying drawings. FIG. 1 shows the basic configuration of a light emission measuring apparatus according to the invention. The apparatus observes in time sequence and measures the fluctuation and intensity of light emission from a sample 8 as an observation object. The light emission measuring apparatus is provided with a controller 1, a parameter setting unit 2, a mode selector 3, a parameter storage 4, a display 5, optics 6, and objective lens 7. The optics 6 and objective lens 7 include a microscopic image obtaining unit (LSM) which obtains a microscopic image under the condition set based on the input parameter, and a light emission measuring unit (FCS) which observes in time sequence light emission in a desired area of the sample 8 corresponding to the microscopic image. The parameter setting unit 2 sets a parameter of the microscopic image obtaining unit used to obtain a microscopic image, and/or a parameter of the light emission measuring unit used for time series observation of light emission in a desired area of the sample 8. The parameter storage 4 stores each parameter set by the parameter setting unit 2. The mode selector 3 selects one of a microscopic image obtaining mode to obtain a microscopic image by the microscopic image obtaining unit, and a light emission measuring mode to observe light emission in a desired area by the light emission measuring unit.

The control unit 1 reads a parameter stored in the parameter storage 4 based on the mode selected by the mode selector 3, inputs the parameter in the microscopic image obtaining unit or light emission measuring unit, and controls the parameter in the microscopic image obtaining unit and/or light emission measuring unit.

Figure 2:
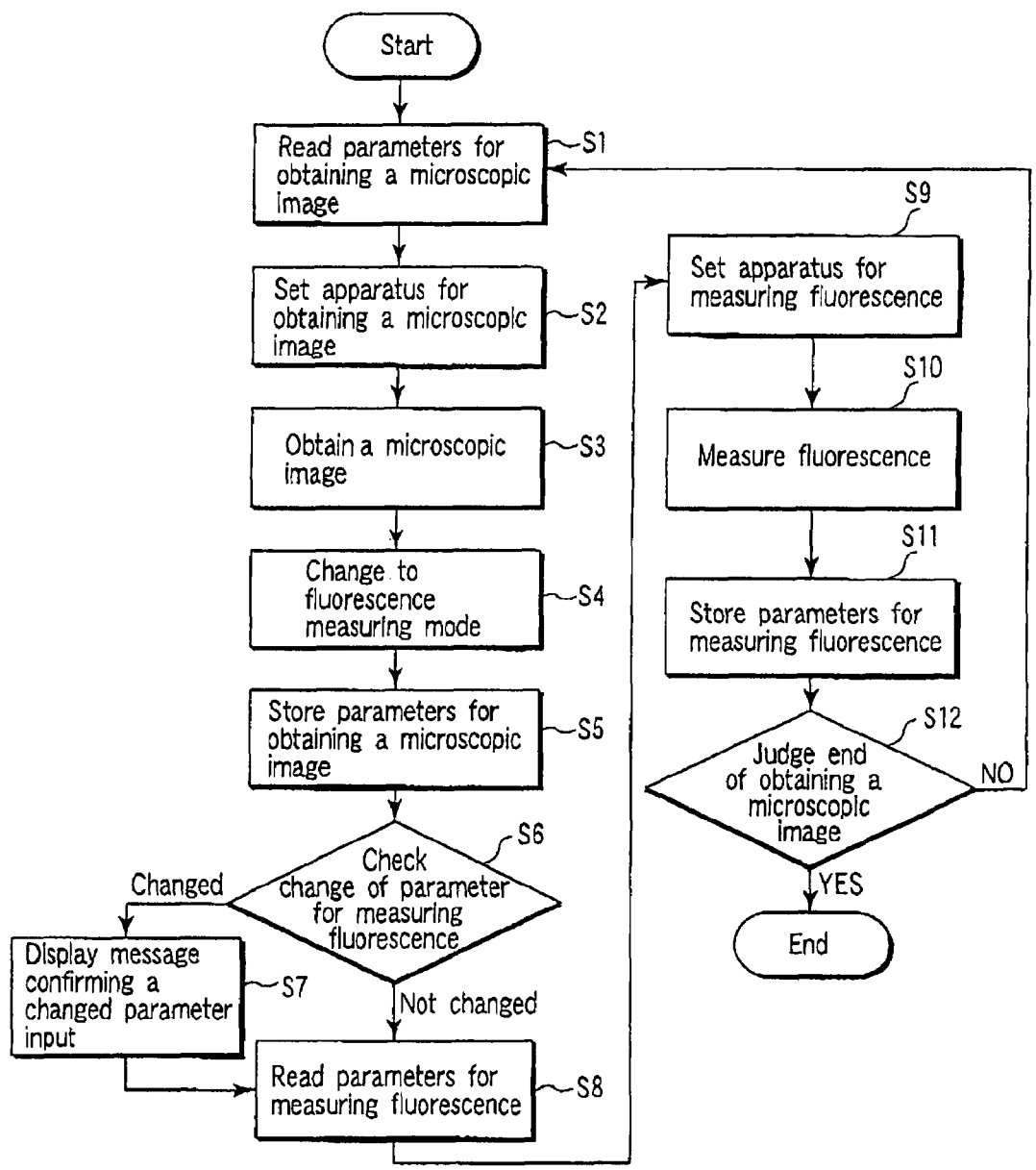
FIG. 2 is a flowchart for explaining the flow of basic measurement of a light emission measuring apparatus according to the invention.

FIG. 2 is a flowchart for explaining the flow of basic measurement of a light emission measuring apparatus according to the invention. First, read a parameter for obtaining a microscopic image (step S1). Then, set the apparatus for obtaining a microscopic image (step S2). Concretely, set a filter, optical path and laser intensity used in the apparatus. Then, obtain a microscopic image by the microscopic image obtaining unit (step S3). Change the mode to a fluorescence measuring mode in response to selection of an FCS tab described later (step S4). Store a parameter for obtaining a microscopic image (step S5). Check whether a parameter for measuring fluorescence is changed, and display a parameter change input confirmation message if the parameter is changed (step S7), and go to step S8. If the parameter is not changed in the step S6, immediately go to the step S8.

In the step S8, read the parameter for measuring fluorescence. Then, set the apparatus for measuring fluorescence (step S9). Concretely, set a filter, optical path and laser intensity used in the apparatus. Then, measure fluorescence (step S10), and store a parameter for measure fluorescence (step S11). Judge whether the microscopic image obtaining step is finished (step S12). When the microscopic image obtaining step is judged finished, finish the processing. If not, return to the step S1, and re-execute the above steps.

FIG. 3 shows the optics of a fluorescence fluctuation measuring apparatus according to an embodiment of the invention.

The optics of this apparatus comprises a laser combiner 101, a laser scanning microscope (LSM) 102, a microscope unit 103, and a fluorescence correlation spectroscopy (FCS) unit 104. The microscope unit 103 functions as an optical microscope. The laser combiner 101 is a light source. The LSM unit 102 is a unit for adding a function to obtain a laser scanning microscopic image. By combining the laser combiner 101, LSM unit 102 and microscope unit 103, a laser scanning microscopic image can be obtained in addition to a microscopic image. The FCS unit 104 is a unit for adding a function to obtain FCS. The FCS unit 104 of this embodiment can also provide a function to obtain cross correlation in addition to the function to obtain FCS. By combining the laser combiner 101, LSM unit 102, microscope unit 103 and FCS unit 104, a microscopic image, laser scanning microscopic image, FCS and cross correlation can be obtained.

The laser combiner 101 has a multi-line argon laser 105, a green helium neon laser 106, a helium neon laser 107, three mechanical shutters 108, three dichroic mirrors 109, and acousto-optic tunable filter (AOTF) 110.

The multi-line argon laser 105 can emit light of 458, 488 and 514 nm. The green helium neon laser can emit light of 543 nm. The helium neon laser 107 can emit light of 633 nm.

A laser with other wavelengths may be used. A glass plate or mirror may be used instead of a dichroic mirror as long as a function of overlapping light described later on the same optical path is not lost. Laser intensity may be controlled by controlling a current applied to a laser without using a mechanical shutter or AOTF.

The LSM unit 102 has first and second galvano scanner mirrors 115 and 116, an exciter dichroic mirror 180, first and second lenses 112 and 114, a pinhole 123, first, second and third dichroic mirrors 125, 128 and 131, first, second and third band-pass filters. 126, 129 and 132, first, second and third photomultipliers 127, 130 and 133, a mercury lamp 118, and a mercury lamp light guide mirror 117.

The exciter dichroic mirror 180, first, second and third dichroic mirrors 125, 128 and 131, and first, second third band-pass filters 126, 129 and 132 are set in respective 6-hole revolver turrets. A dichroic mirror with an optional wavelength and a hand-pass filter can be set in the revolver turret. By using the revolver turret in this way, the dichroic mirrors and band-pass filters can be easily changed.

For example, a dichroic mirror to reflect light of 514 nm and transmit light of other wavelengths, a dichroic mirror to reflect light of 458 and 543 nm and transmit light of other wavelengths, a dichroic mirror to reflect light of 488 and 543 nm and transmit light of other wavelengths, a dichroic mirror to reflect light of 488, 543 and 633 nm and transmit light of other wavelengths, and a beam splitter to reflect 20% of light and transmit 80% of light regardless of wavelengths can be set in the exciter dichroic mirror setting position.

For example, as the first, second and third dichroic mirrors 125, 128 and 131, set a dichroic mirror to reflect light of 560 nm less and transmit light of 560 nm or longer, a dichroic mirror to reflect light of 630 nm or less and transmit light of 630 nm or longer, and a totally reflecting mirror. At the same time, as the first, second and third band-pass filters 126, 129 and 132, set long-pass filters to transmit 505-525, 560-600 and 660 nm or longer, respectively. Then, the first, second and third photomultipliers 127, 130 and 133 can sense fluorescence of 505-525, 560-600 and 660 nm or longer. In addition, a dichroic mirror with optional wavelength characteristic, a totally reflecting mirror, a glass plate for transmitting light and other optional optical elements can be set in the dichroic mirror turret. A band-pass filter of optional wavelength, a glass plate or empty hole for transmitting light, and other optional optical elements can be set in the hand-pass filter turret. Particularly, if the positions for the first and second band-pass filters 126 and 129 are set ready to install long-pass filters to transmit light of 505 and 560 nm, respectively, and the positions for the first and second dichroic mirrors 125 and 128 are set ready to install totally reflecting mirrors as needed, the usability is increased with respect to the above-described band-pass filter set.

The pinhole 123 is variable in diameter. By changing the pinhole diameter, the size and shape of a measuring area of FCS can be changed. The mercury lamp 118 emits light to the mercury lamp light guide mirror 117. When the mirror is placed at the position indicated by a solid line in the drawing, the light from the mercury lamp is not guided to the microscope unit 103. When the mirror is placed at the position indicated by a broken line in the drawing, the light from the mercury lamp is guided to the microscope unit 103.

The microscope unit 103 has a mirror 119 and an objective lens 120. The sample 121 is held by the microscope unit 103. The mirror 119 of the microscope unit is installed as follows. Namely, install a totally reflecting mirror at a dichroic mirror placing position in a dichroic mirror cube for fluorescence observation in an ordinary microscope. Then, the LSM unit 102 can be connected to an optical path for a mercury lamp for fluorescence observation in the microscope unit 103. Ordinary fluorescence observation can be performed by guiding the light for fluorescent image observation from the mercury lamp 118 into the LSM unit 102, and making the dichroic mirror cube of the microscope unit 103 usable for observing a fluorescent image. In this time, a turret for an ordinary dichroic mirror cube can be used when changing the dichroic mirror cube. The objective lens 120 of the microscope unit 103 uses an immersed objective lens of 40× or 60×.

The FCS unit 104 has a fourth dichroic mirror 137, fourth and fifth band-pass filters 138 and 142, fifth and sixth coupling lenses 139 and 143, third and fourth optical fibers 140 and 144, and first and second avalanche photodiodes 141 and 145.

The fourth dichroic mirror 137 is set in a 6-hole revolver turret, and the fourth and fifth band-pass filters 138 and 142 are set in a 4-hole revolver turret. In these revolver turrets, a dichroic mirror and band-pass filter with optional wavelength characteristics can be set. By using the revolver turret in this way, the dichroic mirror and band-pass filter can be easily changed.

The third and fourth optical fibers 140 and 144 use a multimode fiber. By using a multimode fiber, fluorescence can be guided.

The LSM unit 102 and laser combiner 101 are optically connected by the first optical fiber 190 and first coupling lens 111 and second coupling lens 113. The laser combiner 101 and FCS unit 104 are optically connected by the second optical fibers 135 and the third and fourth coupling lenses 134 and 136.

The first optical fiber 190 uses a single mode fiber. By using a single mode fiber, a profile of beam at an emission end is good. A single mode fiber can guide excited light of two or more wavelengths by one optical fiber. The second optical fiber 135 uses a multimode fiber. By using a multimode fiber, fluorescence can be guided. By changing the third and fourth coupling lenses 134 and 136 to appropriate ones, the efficiency of coupling the light emitted from the second optical fiber 135 to the first and second avalanche photodiodes 141 and 145 can be increased.

In this embodiment, a particle of a measuring object can be marked by many kinds of dye such as CFP, YFP, GPF, RFP, DsRed, rhodamine green, rhodamine 6G, Alexa 633, Cy3 and Cy5. The excitation light sources 105-107, exciter dichroic mirror 180, first, second, third and fourth dichroic mirrors 125, 128, 131 and 137, first, second, third, fourth and fifth band-pass filters 126, 129, 132, 138 and 142 can be selected according to a dye to be used.

The functions of the above-described optics will now be explained. Excitation light is emitted from the laser combiner 101, and applied to the sample 121 through the first optical fiber 190, LSM unit 102 and microscope unit 103. Fluorescence from the sample 121 is applied to the FCS unit 104, passing through the microscope unit 103, LSM unit 102 and second optical fiber 135.

The multi-line argon laser 105 emits light of 458, 488 and 514 nm the green helium neon laser 106 emits light of 543 nm. The helium neon laser 107 emits light of 633 nm. The light output from each laser is overlapped on the same optical path by the dichroic mirror 109. By the AOTF 110 and the shutter 108 provided at each laser outlet, light combining desired outputs can be obtained for each laser wavelength. The obtained laser output is coupled to the first optical fiber 190 through the first coupling lens 111.

The laser beam from the first optical fiber 190 is transmitted to the LSM unit 102, and converted to a collimated beam by the second coupling lens 113. The collimated beam is reflected by the exciter dichroic mirror 180, and transmitted to the microscope unit 103 through the first and second galvano scanner mirrors 115 and 116.

The beam applied to the microscope unit 103 is reflected by the mirror 119, and collected on the sample 121 by the objective lens 120. Fluorescence emitted from the sample 121 is collected by the objective lens 120, reflected by the mirror 119, and transmitted to the LSM unit 102.

The fluorescence transmitted to the LSM unit 102 is reflected by the first and second galvano scanner mirrors 115 and 116, passed through the exciter dichroic mirror 180, and collected by a first lens 112. The fluorescence passing through the pinhole 123 provided at a collecting position is converted to a collimated beam by a second lens 114. After passing through the second lens 114, fluorescence of a first wavelength range is reflected by the first dichroic mirror 125, passed through the first band-pass filter 126, and sensed by the first photomultiplier 127. Fluorescence of a second wavelength is passed through the first dichroic mirror 125, reflected by the second dichroic mirror 128, passed through the second band-pass filter 129, and sensed by the second photomultiplier 130, Fluorescence of a third wavelength is passed through the first and second dichroic mirrors 125 and 128, reflected by the third dichroic mirror 131, passed through the third band-pass filter 132, and sensed by the third photomultiplier 133.

The fluorescence passing through the third dichroic mirror 131 is collected by the third coupling lens 134, and coupled to the second optical fiber 135. The laser beam from the second optical fiber 135 is applied to the FCS unit 104, and converted to a parallel beam by the fourth coupling lens 136. The parallel beam is divided by the fourth dichroic mirror 137. Fluorescence with a fourth wavelength range is reflected by the fourth dichroic mirror 137, passed through the fourth band-pass filter 138, and coupled to the third optical fiber 140 through the fifth coupling lens 139. This fluorescence is sensed by the first avalanche photodiode 141. Fluorescence with a fifth wavelength range is passed through the fourth dichroic mirror 137, and coupled to the fourth optical fiber 144 through the sixth coupling lens 143. This fluorescence is received by the second avalanche photodiode 145.

The focal point and observing point of an excited laser beam on the sample 121 are X-axis and Y-axis scanned by the first and second galvano scanner mirrors 115 and 116. Then, the focal point and observing position of the excited laser beam on the sample 121 are two-dimensionally scanned on the sample surface. By adding the movement of the objective lens 120 or sample 121 in the optical axis direction, the focal point and observing position of the excited laser beam on the sample can be three-dimensionally scanned within the sample.

Figure 4:
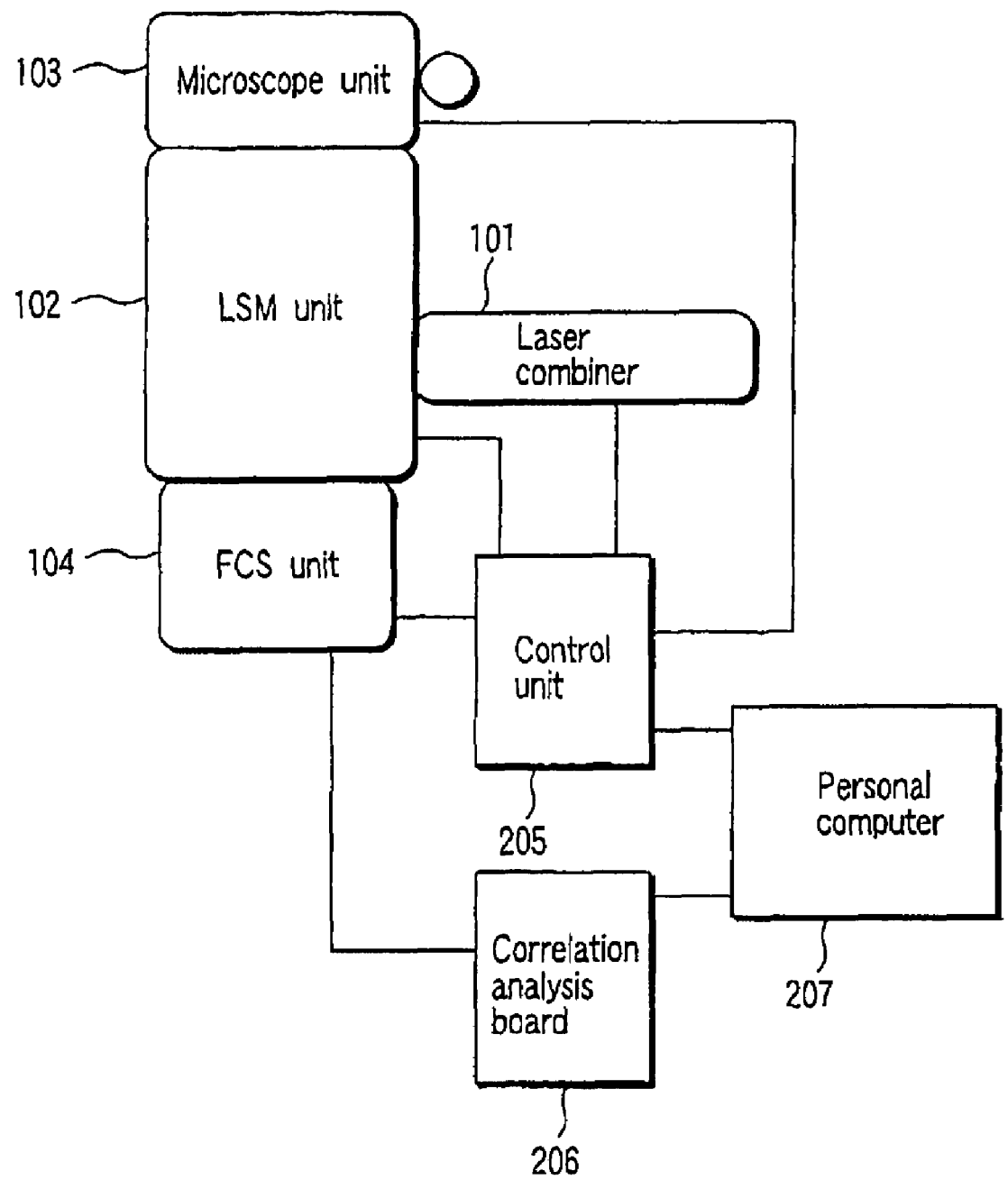
FIG. 4 is a diagram showing the hardware configuration of a fluorescence fluctuation measuring apparatus according to an embodiment of the invention.

FIG. 4 shows the hardware configuration of a fluorescence fluctuation measuring apparatus according to an embodiment of the invention. This apparatus comprises a laser combiner 101, an LSM unit 102, a microscope unit 103, an FCS unit 104, a control unit 205, a correlation analysis board 206, and a personal computer 207.

The control unit 205 can control the motor-driven parts in the laser combiner 101, LSM unit 102, microscope unit 103 and FCS unit 104. In the microscope unit 103, the control unit 205 can control the position of the objective lens 120. In the laser combiner 101, the control unit 205 controls the mechanical shutter 108 and AOTF 110. In the LSM 102, the control unit can control the angles of the first and second galvano scanner mirrors 115 and 116, the position of the first lens 122 or the position of the pinhole 123, the types of first, second and third dichroic mirrors 125, 128 and 131, the types of the first, second and third band-pass filters 126, 129 and 132, the mercury lamp light guide mirror 117, and the mercury lamp shutter. In the FCS unit 104, the control unit can control the type of the fourth dichroic mirror 137, the types of the fourth and fifth band-pass filters 138 and 142, and the positions of the end faces of the third and fourth optical fibers 140 and 144 in the side close to the band-pass filter. The control unit controls these motor-driven parts, and grasps their states through the personal computer 207.

In the FCS unit 104, the first and second avalanche photodiodes 141 and 145 output a light intensity value indicating the intensity of fluorescence of fourth and fifth wavelength ranges. The correlation analysis board 206 performs statistical analysis of the light intensity fluctuations, and outputs the result statistical analysis of light intensity. This light intensity value is output to the personal computer 207. Then, a time correlated operation is performed to calculate a function of autocorrelation of the fluorescence of fourth and fifth wavelength ranges. The calculation result can be displayed as a graph in a monitor display. In this case, a vertical axis represents a correlation value, and a horizontal axis represents a delay time. It is also possible to calculate a function of cross-correlation of the fluorescence of fourth and fifth wavelength ranges.

A sample image is obtained as in a conventional LSM unit. Namely, scan a measuring point three-dimensionally by controlling the objective lens 120 and the first and second galvano scanner mirrors 115 and 116. Detect the intensity of each fluorescence wavelength at each measuring point by the first, second and third photomultipliers 127, 130 and 133, respectively. The fluorescence intensity of each fluorescence wavelength range at each measuring point is processed on the personal computer 207 and visualized as an image. Therefore, a three-dimensional LSM image of each fluorescence wavelength range is obtained. Specify one or more FCS measuring point on this sample image. FCS is measured simultaneously or pseudo-simultaneously at the specified point.

Figure 5:
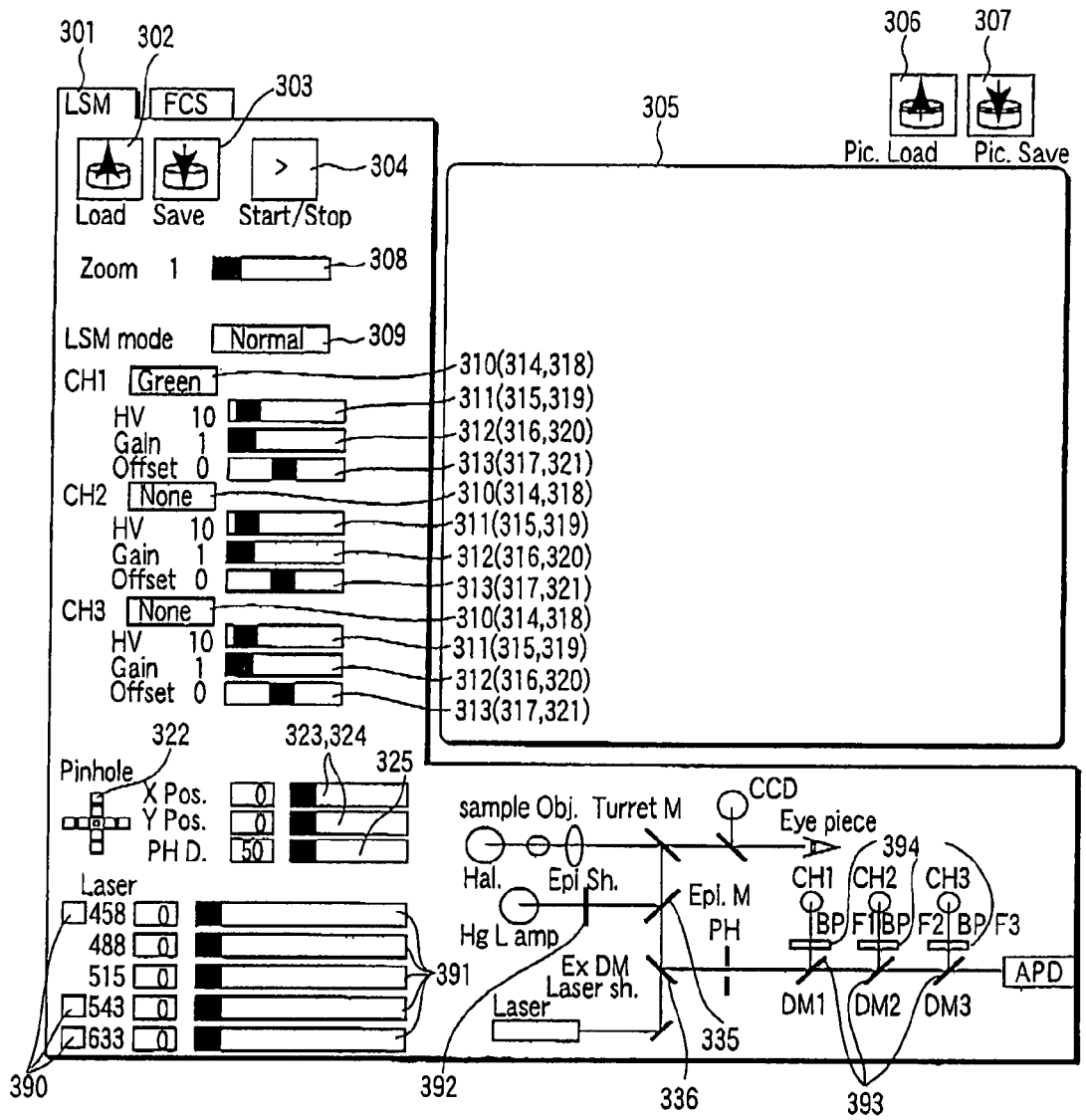
FIG. 5 is a view showing an operation screen of a fluorescence fluctuation measuring apparatus according to an embodiment of the invention, indicating the state that an LSM operation panel is placed on the front side.

The measuring apparatus is controlled by a computer. The operation screen of this embodiment is as shown in FIG. 5 and FIG. 6. FIG. 5 shows the state that the LSM control panel is placed in the front side. FIG. 6 shows the state that the FCS control panel is placed in the front side.

Press the LSM tab 301 in FIG. 5 to place the LSM control panel in the front side. Press the FCS tab 401 in FIG. 6 to place the FCS control panel in the front side. When the LSM tab 301 is pressed in the state that the FCS control panel is placed in the front side, the LSM control panel is placed in the front side, all parameters in the FCS control panel are saved, and the apparatus state is re-set to the LSM measuring state according to all parameters in the LSM control panel used for the previous LSM measurement. When the FCS tab 401 is pressed in the state that the LSM control panel is placed in the front side, the FCS control panel is placed in the front side, all parameters in the LSM control panel are saved, and the apparatus state is re-set to the FCS measuring state according to all parameters in the FCS control panel used for the previous FCS measurement.

The LSM control panel of FIG. 5 will now be explained hereinafter. The LSM control panel can be placed in the front side by pressing the LSM tab 301. All parameters in the LSM control panel can be read and saved by LSM setting read button 302 and LSM setting save button 303. The saved data contents can be easily confirmed even after the end of experiment. All parameters in the LSM control panel include a zoom magnification, an LSM image obtaining speed, display colors of the first/second/third channels, applied voltages of the first/second/third channels, gains of the first/second/third channels, offsets of the first/second/third channels, a relative position of the fluorescence optical axis and the center of the pinhole 123 on the X-axis and Y-axis, a diameter of the pinhole 123, a state of the laser shutter 108 for multi-line argon laser, a state of the laser shutter 108 for green helium neon laser, the state of the laser shutter 108 for helium neon laser, intensity of laser beam of 458 nm, intensity of laser beam of 488 nm, intensity of laser beam of 515 nm, intensity of laser beam of 543 nm, intensity of laser beam of 633 nm, a state of the mercury lamp shutter, a state of the mercury lamp light guide mirror 117, a state of the exciter dichroic mirror 180, states of first/second/third dichroic mirrors 125, 129 and 131, and states of first/second/third band-pass filters 126, 129 and 132.

The signals of the first/second/third channels correspond to the signals from the first/second/third photomultipliers 127, 130 and 133. Start and end of LSM measurement are instructed by an LSM start/end button 304. An LSM image is displayed in an LSM image display window 305. An LSM image is composed of 512 vertical×512 horizontal pixels. The microscopic image can be read and saved by an LSM image read button 306 and an LSM image save button 307. An enlarging magnification of an LSM image can be set to 1-10X by a zoom magnification setting slider 308. An LSM image obtaining speed can be set by an LSM image obtaining speed setting button 309. The speed is selectable from slow, normal and fast. Data of each pixel is obtained at 5,000, 50,000 and 500,000 Hz, respectively at the three speeds. Display colors of first, second and third channels can be selected from Blue, Green and Red by operating the data display color setting buttons 310, 314 and 318 of the first, second and third channel. However, a color already selected for another channel is not selected in order to prevent double color setting. Select None to display no color. Applied voltages of the first/second/third photomultipliers 127, 130 and 133 can be set by the applied voltage setting sliders 311, 315 and 319 of the first/second/third channels. A settable range is 0V to a maximum value durable by a photomultiplier to be used. Gains and offsets of the first/second/third channels can be set by the gain setting sliders 312/316/320 and offset setting sliders 313/317/321 of the first/second/third channels. By these settings, LSM signals of the first/second/third channels can be adjusted and displayed by overlapping. The relative position of the fluorescence optical axis and the center of the pinhole 123 are controlled by a graphical button 322 or pinhole position adjusting sliders for X-axis 323 and Y-axis 324. Then, both X-axis and Y-axis can be moved vertically to the optical axis, in a maximum moving range of over 1 mm, and with resolution finer than 1000 steps. The pinhole diameter can be adjusted by a pinhole diameter adjusting slider 325.

The shutters 108 for the multi-line argon laser 105, green helium neon laser 106 and helium neon laser 107 are opened/closed by shutter control buttons 326, 327 and 328. The intensities of the excited light of 458, 488, 515, 543 and 633 nm are controlled by sliders 329-333 with resolution finer than 1% in a range of 0-100%. In this embodiment, normal observation of fluorescence image by using the mercury lamp 118 is also possible in addition to obtaining LSM image. For this purpose, the mercury lamp shutter is opened/closed by a mercury lamp shutter control button 334. The mercury lamp guide mirror 117 must be set to guide the mercury lamp light. A mercury lamp guide mirror control button 335 is used for this setting. The exciter dichroic mirror 180 for transmitting excited light and reflecting fluorescence must be selected according to wavelengths of excited light and fluorescence. An exciter dichroic mirror control button 336 is used for selecting six mirrors in a turret.

For the first/second/third band-pass filters 126/129/132 and first/second/third dichroic mirrors 125/128/131, respective control buttons are used to select one of six elements in each turret.

Next, the FCS control panel of FIG. 6 will be explained. This control panel can be placed in the front side by pressing the FCS tab 401. All parameters in this control panel can be read and saved by an FCS setting read button 402 and an FCS setting save button 403. The contents of saved data can be easily confirmed even after the end of experiment. All parameters in the control panel include the number of FCS measuring points, positions of FCS measuring points, FCS measuring time at each FCS measuring point, the relative position of the fluorescence optical axis and the center of the pinhole 123 on the X-axis and Y-axis, the diameter of the pinhole 123, a state of the laser shutter 108 for multi-line argon laser, a state of the laser shutter 108 for green helium neon laser, a state of the laser shutter 108 for helium neon laser, intensity of laser beam of 458 nm, intensity of laser beam of 488 nm, intensity of laser beam of 515 nm, intensity of laser beam of 543 nm, intensity of laser beam of 633 nm, a state of the mercury lamp shutter, a state of the mercury lamp light guide mirror 117, a state of the exciter dichroic mirror 180, states of first/second/third dichroic mirrors 125, 128 and 131, and states of first/second/third band-pass filters 126, 129 and 132. In this embodiment, when measuring FCS at two or more measuring points, first measure FCS sequentially at each point (as one cycle), and perform this cycle by two or more times. By executing one cycle of measurement in very short time, FCS is measured pseudo-simultaneously at each measuring point. Start and end of FCS measurement are instructed by an FCS operation start/end button 404. The number of FCS measuring points can be set to 1-4 points by an FCS measuring point setting button 408. A position on an LSM image at each FCS measuring point can be set by an FCS measuring point position setting button 409 with resolution of 1 pixel in a range of an LSM image. An LSM image is displayed in an LSM image display window 405. An FCS measuring point is also displayed as a "+" mark on this image. An FCS measuring point position can also be set by moving the "+" by drag-and-drop of a mouse. Coordinates of each measuring point can be displayed by adjusting a mouse cursor to the above mark. The LSM image can be read and saved by an LSM image read button 406 and an LSM image save button 407. In this time, an LSM image and FCS measuring point position display are overlapped, and read and saved as an image. The functions of other operation buttons 422-442 are similar to the functions of the LSM measurement setting buttons 322-342, but generally for setting FCS measurement.

In this embodiment, one or more FCS measuring point is specified on a sample image by using the above configuration, and FCS measurement is performed simultaneously or pseudo-simultaneously at a specified point. Then, timing of a change in the measured substance diffusing time at each point can be known. Self-correlation between measuring points is compared by the FCS data obtained simultaneously or pseudo-simultaneously at two or more points. Then, a change in the measured substance diffusing time at a point A is compared with that at a point B, and a speed of conveying the change between two the points can be known.

In this embodiment, it is possible to use a cell as a sample, and to measure a change in the protein diffusion time in a cell. This change in the diffusion time indicates the state of coupling a measured protein to other protein, overlapped state of a measured protein, and three-dimensional structure of measured protein. Transmission of information in a cell is performed through such a change, and the state of information transfer in a cell or between cells can be known by tracking the change in the diffusion speed. Speed of information transfer between points can be known by performing the measurement simultaneously or pseudo-simultaneously at more than one point in a cell.

The configuration of the embodiment of the invention can be modified or changed. For example, more than one excitation optics and detection optics may be used, and a detected signal may be processed in various ways, thereby obtaining special effects. Particularly, for reading and saving LSM and FCS states, various settings and controls in the FCS unit or microscope may be used in addition to those mentioned in this embodiment.

The invention is not limited to the above-mentioned embodiments. Various changes are possible in a practical stage without changing the essential characteristics.

The above-mentioned embodiments include various states of the invention. The invention will be embodied in various forms by appropriately combining the components disclosed hereinbefore. For example, even if some components are deleted from the components disclosed in the embodiments, the problems to be solved by the invention can be solved. If the effects of the invention are obtained, the configuration with some components deleted can be embodied as a form of the invention.

INDUSTRIAL APPLICABILITY

According to the present invention. It is possible to eliminate the time for various setting when switching measurements of microscopic image and fluorescence fluctuation, and improve convenience of the apparatus.

The invention claimed is:

1. A light emission measuring apparatus for observing and measuring light emission from a sample as an observation object in time series, comprising:
   a microscopic image obtaining unit which obtains a microscopic image of a sample under conditions set based on input parameters;
   a light emission measuring unit which observes light emission in a desired area of the sample corresponding to the microscopic image in time series under conditions set by input parameters;
   a parameter setting unit which sets parameters of the microscopic image obtaining unit used for obtaining the microscopic image and/or parameters of the light emission measuring unit used for observing light emission in a desired area of the sample in time series;
   a parameter storage which stores parameters set by the parameter setting unit;
   a mode selector which selects one of a microscopic image obtaining mode for obtaining the microscopic image by the microscopic image obtaining unit, and a light emission measuring mode for observing light emission in the desired area by the light emission measuring unit; and
   a control unit which reads parameters stored in the storage based on a mode selected by the mode selector, inputs the parameter to the microscopic image obtaining unit or the light emission measuring unit, and controls the microscopic image obtaining unit and/or the light emission measuring unit.

2. The light emission measuring apparatus according to claim 1, wherein the light emission measuring apparatus measures fluctuation of light emission.

3. The light emission measuring apparatus according to claim 1, wherein the light emission is fluorescence.

4. The light emission measuring apparatus according to claim 3, wherein the microscopic image obtaining unit is a laser scanning microscope unit.

5. The light emission measuring apparatus according to claim 4, wherein the laser scanning microscope unit is a confocal type.

6. The light emission measuring apparatus according to claim 3, wherein the parameters input to the microscopic image obtaining unit are parameters related to optics of the microscopic image obtaining unit.

7. The light emission measuring apparatus according to claim 6, wherein the parameters input to the microscopic image obtaining unit are parameters related to a lens and/or a filter and/or a pinhole of the microscopic image obtaining unit.

8. The light emission measuring apparatus according to claim 3, wherein the parameters input to the microscopic image obtaining unit are stored in the parameter storage at the end of microscopic image obtaining mode.

9. The light emission measuring apparatus according to claim 3, wherein the parameters input to the microscopic image obtaining unit are read from the parameter storage at the start of the microscopic image obtaining mode.

10. The light emission measuring apparatus according to claim 3, wherein the parameters related to the light emission measuring unit input to the parameter storage are interlocked with setting of the microscopic image obtaining unit.

11. The light emission measuring apparatus according to claim 3, wherein the parameters input to the light emission measuring unit are parameters related to optics of the light emission measuring unit.

12. The light emission measuring apparatus according to claim 11, wherein the parameters input to the microscopic image obtaining unit are parameters related to optics defining an observation area of the microscopic image obtaining unit.

13. The light emission measuring apparatus according to claim 12, wherein the observation area is more than one.

14. The light emission measuring apparatus according to claim 11, wherein the parameters input to the light emission measuring unit are parameters related to a lens and/or a filter and/or mirror and/or AOTF and/or a pinhole of the light emission measuring unit.

15. The light emission measuring apparatus according to claim 3, wherein the parameters input to the light emission measuring unit are stored in the parameter storage at the end of the light emission measuring mode.

16. The light emission measuring apparatus according to claim 3, wherein the parameters input to the light emission measuring unit are read from the parameter storage at the start of the light emission measuring mode.

17. The light emission measuring apparatus according to claim 3, wherein the parameters related to the microscopic image obtaining unit input to the parameter storage are interlocked with setting of the light emission measuring unit.

18. The light emission measuring apparatus according to claim 3, wherein when the parameters related to the microscopic image obtaining unit are changed, a display is made for confirming a changed input to the light emission measuring unit at the start of the light emission measuring mode.

19. The light emission measuring apparatus according to claim 3, wherein the microscopic image obtaining unit and light emission measuring unit share a part of optics.

20. The light emission measuring apparatus according to claim 19, wherein the parameters input to the microscopic image obtaining unit and light emission measuring unit include parameters related to optics shared by the microscopic image obtaining unit and light emission measuring unit.

21. The light emission measuring apparatus according to claim 3, wherein the parameter setting unit includes an observing position setter for setting a light emission observing area according to the microscopic image.

22. The light emission measuring apparatus according to claim 3, further comprising an output unit for displaying or printing observation results.

23. The light emission measuring apparatus according to claim 22, wherein the output unit performs the display by relating to parameters.

24. The light emission measuring apparatus according to claim 3, further comprising a data processor for performing time correlated operations.

25. The light emission measuring apparatus according to claim 24, further comprising a display unit for displaying results of the time correlated operations as a graph.

26. The light emission measuring apparatus according to claim 25, wherein the graph takes a correlation value on a vertical axis, and a delay time on a horizontal axis.

27. The light emission measuring apparatus according to claim 25, wherein the display unit performs the display by correlating with any one of the parameters.

28. A light emission measuring method for observing and measuring light emission from a sample as an observing object in time series, comprising:
   a microscopic image obtaining step for obtaining a microscopic image of a sample under conditions set based on input parameters;
   a light emission measuring step for observing light emission in a desired area of the sample corresponding to the microscopic image in time series under conditions set by input parameters;
   a parameter setting step for setting parameters of the microscopic image obtaining unit used for obtaining the microscopic image and/or parameters of the light emission measuring unit used for observing light emission in a desired area of the sample in time series;
   a parameter storing step for storing parameters set in the parameter setting step;
   a mode selecting step for selecting one of a microscopic image obtaining mode for obtaining the microscopic image in the microscopic image obtaining step, and a light emission measuring mode for observing light emission in the desired area in the light emission measuring step; and
   a control step for reading parameters stored in the storing step based on a mode selected by the mode selecting step, and controlling the microscopic image obtaining step and/or the light emission measuring step.

29. The light emission measuring method according to claim 28, wherein the light emission measuring method includes measuring fluctuation of the light emission.

* * * * *